(12) United States Patent
Youn

(10) Patent No.: US 9,096,867 B2
(45) Date of Patent: Aug. 4, 2015

(54) CODON OPTIMIZED SODIUM-IODIDE SYMPORTER GENE AND ITS USE

(71) Applicant: SNU R&DB FOUNDATION, Seoul (KR)

(72) Inventor: Hyewon Youn, Seoul (KR)

(73) Assignee: SNU R&DB FOUNDATION, Seoul (KR)

(*) Notice: Subject to any disclaimer, the term of this patent is extended or adjusted under 35 U.S.C. 154(b) by 0 days.

(21) Appl. No.: 13/920,692

(22) Filed: Jun. 18, 2013

(65) Prior Publication Data

US 2014/0038286 A1 Feb. 6, 2014

(30) Foreign Application Priority Data

Jun. 19, 2012 (KR) .................. 10-2012-0065546

(51) Int. Cl.

| | | |
|---|---|---|
| *C12P 21/04* | (2006.01) | |
| *C07K 14/705* | (2006.01) | |
| *C12P 21/06* | (2006.01) | |
| *C12N 1/00* | (2006.01) | |
| *C12N 5/00* | (2006.01) | |
| *C12N 5/071* | (2010.01) | |
| *C12N 15/00* | (2006.01) | |
| *C12N 15/85* | (2006.01) | |
| *C07H 19/06* | (2006.01) | |
| *C07H 19/16* | (2006.01) | |

(52) U.S. Cl.
CPC .............. *C12N 15/85* (2013.01); *C07K 14/705* (2013.01); *C12N 2800/22* (2013.01)

(58) Field of Classification Search
None
See application file for complete search history.

(56) References Cited

U.S. PATENT DOCUMENTS

2006/0004191 A1 1/2006 Jhiang et al.
2012/0027676 A1 2/2012 Ho et al.

OTHER PUBLICATIONS

Dingli et al., "In Vivo Imaging and Tumor Therapy With the Sodium Iodide Symporter" 90 Journal of Cellular Biochemistry 1079-1086 (2003).*
Codon Usage Database (Data source NCBI—GenBank (Jun. 15, 2007).*
Gustafsson et al., "Codon bias and heterologous protein expression" 22(7) TRENDS in Biotechnology 346-353 (2004).*
P. A. Smanik et al., "Cloning of the Human Sodium Iodide Symporter", Biochemical and Biophysical Research Communications 226, 339-345 (1996), Article No. 1358, vol. 226, No. 2, 1996.

* cited by examiner

*Primary Examiner* — Celine Qian
*Assistant Examiner* — Nancy J Leith
(74) *Attorney, Agent, or Firm* — Vorys, Sater, Seymour and Pease LLP; Mihsun Koh

(57) ABSTRACT

The present disclosure provides a polynucleotide which is codon optimized for the efficient expression in a eukaryotic cell, a plasmid and a eukaryotic cell comprising the same. The modification resulted in the efficient expression of NIS in eukaryotic cells and the enhancement of the function of NIS by glycosylation. Thus modified polynucleotide encoding NIS of the present disclosure is useful as imaging reporter for gene, viral and/or cell based therapies.

7 Claims, 19 Drawing Sheets

Codon Frequency Distribution (CFD) of optimized NIS

SEQUENCE LISTING

<160> NUMBER OF SEQ ID NOS: 7

<210> SEQ ID NO 1
<211> LENGTH: 1938
<212> TYPE: DNA
<213> ORGANISM: Artificial Sequence
<220> FEATURE:
<221> NAME/KEY: misc_feature
<222> LOCATION: (1)..(1929)
<223> OTHER INFORMATION: Homo sapiens NIS coding sequence

<400> SEQUENCE: 1

```
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcaccggg ggccggcgcc tggcggccct gcccgtgggc     180
ctgtcgctgt ctgccagctt catgtcggcc gtgcaggtgc tgggcgtgcc gtcggaggcc     240
tatcgctatg gcctcaagtt cctctggatg tgcctgggcc agcttctgaa ctcggtcctc     300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gctcctgtcc accggaatta tctgcacctt ctacacggct     540
gtgggcggca tgaaggctgt ggtctggact gatgtgttcc aggtcgtggt gatgctaagt     600
ggcttctggg ttgtcctggc acgcggtgtc atgcttgtgg gcgggccccg ccaggtgctc     660
acgctggccc agaaccactc ccggatcaac ctcatggact ttaaccctga cccgaggagc     720
cgctatacat tctggacttt tgtggtgggt ggcacgttgg tgtggctctc catgtatggc     780
gtgaaccagg cgcaggtgca gcgctacgtg gcttgccgca cagagaagca ggccaagctg     840
gccctgctca tcaaccaggt cggcctgttc ctgatcgtgt ccagcgctgc ctgctgtggc     900
atcgtcatgt ttgtgttcta cactgactgc gaccctctcc tctggggcg catctctgcc     960 ccagaccagt acatgcctct gctggtgctg gacatcttcg aagatctgcc tggagtcccc    1020
gggcttttcc tggcctgtgc ttacagtggc acctcagca cagcatccac cagcatcaat    1080
gctatggctg cagtcactgt agaagacctc atcaaacctc ggctgcggag cctggcaccc    1140
aggaaactcg tgattatctc caagggctc tcactcatct acggatcggc ctgtctcacc    1200
gtggcagccc tgtcctcact gctcggagga ggtgtccttc agggctcctt caccgtcatg    1260
ggagtcatca gcggccccct gctgggagcc ttcatcttgg aatgttcct gccggcctgc    1320 aacacaccgg gcgtcctcgc gggactaggc gcgggcttgg cgctgtcgct gtgggtggcc    1380
ttgggcgcca cgctgtaccc acccagcgag cagaccatga gggtcctgcc atcgtcggct    1440
gcccgctgcg tggctctctc agtcaacgcc tctgccctcc tggacccggc tctcctcct    1500
```

```
gctaacgact ccagcagggc ccccagctca ggaatggacg ccagccgacc cgccttagct    1560
gacagcttct atgccatctc ctatctctat tacggtgccc tgggcacgct gaccactgtg    1620
ctgtgcggag ccctcatcag ctgcctgaca ggccccacca agcgcagcac cctggccccg    1680
ggattgttgt ggtgggacct cgcacggcag acagcatcag tggcccccaa ggaagaagtg    1740
gccatcctgg atgacaactt ggtcaagggt cctgaagaac tccccactgg aaacaagaag    1800 cccccctggct tcctgcccac caatgaggat cgtctgtttt tcttggggca gaaggagctg    1860
gagggggctg gctcttggac cccctgtgtt ggacatgatg gtggtcgaga ccagcaggag    1920
acaaacctct gagttaac                                                  1938
```

<210> SEQ ID NO 2
<211> LENGTH: 1946
<212> TYPE: DNA
<213> ORGANISM: Artificial Sequence
<220> FEATURE:
<221> NAME/KEY: misc_feature
<222> LOCATION: (1)..(1929)
<223> OTHER INFORMATION: Homo sapiens NIS coding sequence

<400> SEQUENCE: 2

```
atggaagccg tggaaaccgg cgagaggccc accttcggcg cctgggatta tggcgtgttc      60
gccctgatgc tgctggtgtc caccggcatc ggcctgtggg tgggactggc cagaggcggc     120
cagagaagcg ccgaggactt cttcaccggc ggcagaaggc tggccgccct gcctgtggga     180
ctgagcctga cgccagcttc atgagcgcc gtgcaggtgc tggagtgcc cagcgaggcc      240 tacagatacg gcctgaagtt cctgtggatg tgcctgggcc agctgctgaa cagcgtgctg     300
accgccctgc tgttcatgcc cgtgttctac cggctgggcc tgaccagcac ctacgagtac     360
ctggaaatgc ggttcagcag agccgtgcgg ctgtgcggca ccctgcagta catcgtggcc     420
accatgctgt acacaggcat cgtgatctac gcccctgccc tgatcctgaa ccaggtgaca     480
ggcctggaca tctgggcctc cctgctgagc accggcatca tctgcacctt ctacaccgcc     540
gtgggcggca tgaaggccgt ggtgtggacc gacgtgttcc aggtggtggt gatgctgagc     600
ggcttctggg tggtgctggc tcgggcgtg atgctggtgg aggccctag acaggtgctg     660 accctggccc agaaccacag ccggatcaac ctgatggact tcaaccccga ccccagaagc     720
cggtacacct tctggacctt cgtggtggga ggaaccctgg tgtggctgtc tatgtacggc     780
gtgaaccagg cccaggtgca gagatacgtg gcctgccgga ccgagaagca ggccaagctg     840
gccctgctga tcaaccaggt gggactgttc ctgatcgtgt ccagcgccgc ctgctgcgga     900
atcgtgatgt tcgtgttcta caccgactgc gacccctgc tgctgggcag aatcagcgcc     960
cctgaccagt acatgcccct gctggtgctg acatcttcg gaggacctgcc tggcgtgccc    1020 ggcctgttcc tggcctgtgc ctacagcggc acactgagca ccgccagcac ctccatcaac    1080
gccatggccg ccgtgaccgt ggaagatctg atcaagcccc ggctgcggag cctggccccc    1140
agaaagctgg tgatcatcag caagggcctg agcctgatct acggcagcgc ctgtctgacc    1200
gtggccgctc tgagttctct gctgggcgga ggcgtgctgc agggcagctt taccgtgatg    1260
ggcgtgatca gcgcccact gctgggcgcc ttcatcctgg gcatgtttct gcccgcctgc    1320 aacaccctg gcgtgctggc tggactggga gccggactgg ctctgtctct gtgggtggcc    1380
ctgggcgcca ccctgtaccc tccaagcgag cagaccatgc gggtgctgcc tagcagcgcc    1440
gccagatgtg tggccctgtc cgtgaatgcc agcggcctgc tggatcctgc cctgctgccc    1500
```

-continued

```
gccaacgaca gcagcagagc ccccagcagc ggcatggatg cctctagacc tgccctggcc    1560
gacagcttct acgccatcag ctacctgtac tacggcgccc tgggcaccct gaccacagtg    1620
ctgtgtggcg ccctgatcag ctgcctgacc ggccccacca agagaagcac actggcccct    1680
ggcctgctgt ggtgggacct ggctagacag acagccagcg tggcccccaa agaagaggtg    1740
gccatcctgg acgacaacct ggtgaaaggc cccgaggaac tgcccaccgg caacaagaag    1800 cccccctggct tcctgcccac caacgaggac cggctgttct tcctgggcca aaagagctg    1860 gaaggcgccg aagctggac ccctgtgtg ggacacgacg cggcaggga ccagcaggaa     1920 acaaatctgt gagttaactt aattaa                                         1946
```

<210> SEQ ID NO 3
<211> LENGTH: 643
<212> TYPE: PRT
<213> ORGANISM: Homo sapiens

<400> SEQUENCE: 3

```
Met Glu Ala Val Glu Thr Gly Glu Arg Pro Thr Phe Gly Ala Trp Asp
 1               5                  10                  15

Tyr Gly Val Phe Ala Leu Met Leu Leu Val Ser Thr Gly Ile Gly Leu
                20                  25                  30

Trp Val Gly Leu Ala Arg Gly Gly Gln Arg Ser Ala Glu Asp Phe Phe
            35                  40                  45

Thr Gly Gly Arg Arg Leu Ala Ala Leu Pro Val Gly Leu Ser Leu Ser
        50                  55                  60

Ala Ser Phe Met Ser Ala Val Gln Val Leu Gly Val Pro Ser Glu Ala
 65                  70                  75                  80

Tyr Arg Tyr Gly Leu Lys Phe Leu Trp Met Cys Leu Gly Gln Leu Leu
                85                  90                  95

Asn Ser Val Leu Thr Ala Leu Leu Phe Met Pro Val Phe Tyr Arg Leu
            100                 105                 110

Gly Leu Thr Ser Thr Tyr Glu Tyr Leu Glu Met Arg Phe Ser Arg Ala
        115                 120                 125

Val Arg Leu Cys Gly Thr Leu Gln Tyr Ile Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                165                 170                 175

Phe Tyr Thr Ala Val Gly Gly Met Lys Ala Val Trp Thr Asp Val
            180                 185                 190

Phe Gln Val Val Met Leu Ser Gly Phe Trp Val Leu Ala Arg
        195                 200                 205

Gly Val Met Leu Val Gly Gly Pro Arg Gln Val Leu Thr Leu Ala Gln
    210                 215                 220

Asn His Ser Arg Ile Asn Leu Met Asp Phe Asn Pro Asp Pro Arg Ser
225                 230                 235                 240

Arg Tyr Thr Phe Trp Thr Phe Val Val Gly Gly Thr Leu Val Trp Leu
                245                 250                 255

Ser Met Tyr Gly Val Asn Gln Ala Gln Val Gln Arg Tyr Val Ala Cys
            260                 265                 270

Arg Thr Glu Lys Gln Ala Lys Leu Ala Leu Leu Ile Asn Gln Val Gly
        275                 280                 285

Leu Phe Leu Ile Val Ser Ser Ala Ala Cys Cys Gly Ile Val Met Phe
```

```
                290                 295                 300
Val Phe Tyr Thr Asp Cys Asp Pro Leu Leu Leu Gly Arg Ile Ser Ala
305                 310                 315                 320

Pro Asp Gln Tyr Met Pro Leu Val Leu Asp Ile Phe Glu Asp Leu
                325                 330                 335

Pro Gly Val Pro Gly Leu Phe Leu Ala Cys Ala Tyr Ser Gly Thr Leu
                340                 345                 350

Ser Thr Ala Ser Thr Ser Ile Asn Ala Met Ala Ala Val Thr Val Glu
                355                 360                 365

Asp Leu Ile Lys Pro Arg Leu Arg Ser Leu Ala Pro Arg Lys Leu Val
            370                 375                 380

Ile Ile Ser Lys Gly Leu Ser Leu Ile Tyr Gly Ser Ala Cys Leu Thr
385                 390                 395                 400

Val Ala Ala Leu Ser Ser Leu Leu Gly Gly Val Leu Gln Gly Ser
                    405                 410                 415

Phe Thr Val Met Gly Val Ile Ser Gly Pro Leu Leu Gly Ala Phe Ile
                420                 425                 430

Leu Gly Met Phe Leu Pro Ala Cys Asn Thr Pro Gly Val Leu Ala Gly
            435                 440                 445

Leu Gly Ala Gly Leu Ala Leu Ser Leu Trp Val Ala Leu Gly Ala Thr
            450                 455                 460

Leu Tyr Pro Pro Ser Glu Gln Thr Met Arg Val Leu Pro Ser Ser Ala
465                 470                 475                 480

Ala Arg Cys Val Ala Leu Ser Val Asn Ala Ser Gly Leu Leu Asp Pro
                485                 490                 495

Ala Leu Leu Pro Ala Asn Asp Ser Ser Arg Ala Pro Ser Ser Gly Met
            500                 505                 510

Asp Ala Ser Arg Pro Ala Leu Ala Asp Ser Phe Tyr Ala Ile Ser Tyr
            515                 520                 525

Leu Tyr Tyr Gly Ala Leu Gly Thr Leu Thr Thr Val Leu Cys Gly Ala
            530                 535                 540

Leu Ile Ser Cys Leu Thr Gly Pro Thr Lys Arg Ser Thr Leu Ala Pro
545                 550                 555                 560

Gly Leu Leu Trp Trp Asp Leu Ala Arg Gln Thr Ala Ser Val Ala Pro
                565                 570                 575

Lys Glu Glu Val Ala Ile Leu Asp Asp Asn Leu Val Lys Gly Pro Glu
                580                 585                 590

Glu Leu Pro Thr Gly Asn Lys Lys Pro Pro Gly Phe Leu Pro Thr Asn
            595                 600                 605

Glu Asp Arg Leu Phe Phe Leu Gly Gln Lys Glu Leu Glu Gly Ala Gly
            610                 615                 620

Ser Trp Thr Pro Cys Val Gly His Asp Gly Gly Arg Asp Gln Gln Glu
625                 630                 635                 640

Thr Asn Leu

<210> SEQ ID NO 4
<211> LENGTH: 20
<212> TYPE: DNA
<213> ORGANISM: Artificial Sequence
<220> FEATURE:
<223> OTHER INFORMATION: amplification primer for NIS: forward

<400> SEQUENCE: 4
tgggcggcat gaaggcygtg                                           20
```

```
<210> SEQ ID NO 5
<211> LENGTH: 20
<212> TYPE: DNA
<213> ORGANISM: Artificial Sequence
<220> FEATURE:
<223> OTHER INFORMATION: amplification primer for NIS: reverse

<400> SEQUENCE: 5
crctgtaggc acaggccagg                                                   20

<210> SEQ ID NO 6
<211> LENGTH: 20
<212> TYPE: DNA
<213> ORGANISM: Artificial Sequence
<220> FEATURE:
<223> OTHER INFORMATION: amplification primer for GAPDH: forward

<400> SEQUENCE: 6
gagaaggctg gggctcattt                                                   20

<210> SEQ ID NO 7
<211> LENGTH: 18
<212> TYPE: DNA
<213> ORGANISM: Artificial Sequence
<220> FEATURE:
<223> OTHER INFORMATION: amplification primer for GAPDH: reverse

<400> SEQUENCE: 7
ccttccgtgt ccccactg                                                     18
```

CODON OPTIMIZED SODIUM-IODIDE SYMPORTER GENE AND ITS USE

CROSS-REFERENCE TO RELATED APPLICATIONS

This application claims the benefit of Korean Patent Application NO. 2012-0065546 filed Jun. 19, 2012 in the Korean Intellectual Property Office; disclosure of which is incorporated herein by reference.

SEQUENCE LISTING

The Sequence Listing submitted in txt format (.txt), named "SequenceListing_YOUN.txt" (originally created on Jun. 18, 2013, 11.2 KB; and revised on Sep. 26, 2013, 12 KB;); is incorporated herein by reference.

BACKGROUND OF INVENTION

1. Field of the Invention

The present disclosure relates to a Sodium-Iodide Symporter gene optimized for the expression in eukaryotic cells and its uses.

2. Description of the Related Art

Generally in cells genes are transcribed from DNA to mRNA; which in turn are translated into proteins. During the translational process; tRNAs which carry 3 bases corresponding to each codon of a single amino acid are involved and each amino acid is encoded by more than one codon. Due to this codon degeneracy; the frequency of codon usage varies depending on the types of cells where genes are expressed. Therefore; DNA sequence is needed to be modified by synonymous nucleotide substitutions without altering the amino acid sequence of the encoded protein for the efficient expression of recombinant genes in heterologous systems.

Sodium Iodide Symporter (NIS) is a transmembrane glycoprotein with a MW of 87 kDa and 12 transmembrane domains; which transports two sodium cations for each iodide anion into cells. NIS mediated uptake of iodide into follicular cells of the thyroid gland is the first step in the synthesis of thyroid hormone resulting in 20-40 higher concentration of iodide in the thyroid.

The gene coding for NIS was first isolated in rats by Dai et al. (Dai et al.; Nature; 1996; 379: 458-460); followed by the isolation of Human NIS (hNIS) gene by Smanik et al. (Smanik et al.; Biochem. Biophysic. Res. Comm 226: 339-345; 1997).

U.S. Patent Publication 2006-0004191 relates to modified sodium iodide symporter proteins and genes for imaging and cancer therapy and discloses modified NIS proteins having a net electrostatic charge more positive than that of corresponding wild type NIS proteins.

U.S. Patent Publication 2012-0027676 relates to modified sodium iodide symporter proteins and uses thereof and discloses the modified NIS proteins in the cells results in higher intracellular levels of a substrate of a NIS protein than does the expression of the same amount of a wild-type NIS protein.

However; there exist needs to develop modified NIS genes optimized for the efficient expression in eukaryotic cells particularly in human cells for the treatment of thyroid disease and radionuclide gene therapy and molecular imaging using NIS.

SUMMARY OF THE INVENTION

In one aspect the present disclosure provides a polynucleotide encoding a sodium-iodide symporter (NIS) protein; the polynucleotide is codon optimized for the expression in a eukaryotic cell. In one embodiment, the polypeptide is codon optimized in the nucleotide coding for the 8$^{th}$ transmembrane domain corresponding to amino acid residues 286-308 and the 5$^{th}$ transmembrane domain corresponding to 163-182, and C-terminal region corresponding to 550-643; one or more of the phosphorylation sites of Ser-43, Thr-49, Ser-227, Lys-577, and Ala-581; and one or more of the N-glycosylation sites of Asn-225 Asn-489 and Asn-502, wherein the amino acid residue numbers correspond to the residue in SEQ ID NO:3.

In other embodiment, the polynucleotide has at least one of the following modification in the sequence as disclosed in SEQ ID NO: 1: 6th: G→A; 15 the G→A; 22th: G→C; 24th: A→G; 25th: C→A; 39th: A→C; 48th: C→T; 51th: C→T; 54th: G→C; 57th: C→G; 60th: T→C; 66th: C→G; 72th: C→G; 84th: T→C; 93th: G→C; 102th: C→G; 105th: G→A; 111th: T→C; 112th: C→A; 114th: G→A; 120th: G→C; 124th: C→A; 126th: C→A; 132th: T→C; 150th: G→C; 154th: C→A; 156th: G→A; 157th: C→A; 159th: C→G; 165th: G→C; 174th: C→T; 180th: C→A; 184th: T→A; 185th: C→G; 186th: G→C; 190th: T→A; 191th: C→G; 192th: T→C; 205th: T→A; 206th: C→G; 207th: G→C; 225th: C→A; 231th: C→G; 232th: T→A; 233th: C→G; 234th: G→C; 243th: T→C; 244th: C→A; 246th: C→A; 249th: T→C; 255th: C→G; 264th: C→G; 285th: T→G; 292th: T→A; 293th: C→G; 294th: G→C; 297th: C→G; 300th: C→G; 312th: C→G; 324th: C→G; 333th: C→G; 342th: C→G; 366th: G→A; 372th: C→G; 379th: C→A; 381th: C→A; 384th: A→C; 393th: C→G; 399th: G→C; 402th: T→C; 403th: T→C; 414 th: T→C; 417th: A→G; 423th: G→C; 435th: C→A; 444th: A→C; 456th: G→T; 462th: C→G; 474th: A→G; 480th: C→A; 483th: G→C; 498th: G→C; 501th: G→C; 504th: C→G; 508th: T→A; 509th: C→G; 516th: A→C; 519th: T→C; 537th: G→C; 540th: T→C; 558th: T→C; 564th: C→G; 570th: T→C; 573th: T→C; 585th: C→G; 597th: A→G; 600th: T→C; 612th: T→G; 615 th: C→G; 621th: A→T; 624th: C→G; 627th: T→C; 630th: C→G; 636th: T→G; 642th: C→A; 645th: G→C; 648th: C→T; 649th: C→A; 651th: C→A; 660th: C→G; 663th: G→C; 679th: T→A; 680th: C→G; 693th: C→G; 702th: T→C; 708th: T→C; 714th: G→C; 717th: G→A; 723th: C→G; 726th: T→C; 729th: A→C; 738th: T→C; 741th: T→C; 750th: T→A; 753th: C→A; 756th; G→C; 757th: T→C; 768th: C→A; 771th: C→T; 777th: T→C; 792th: G→C; 802th: C→A; 804th: C→A; 813th: T→C; 819th: C→G; 822th: A→C; 849 th: C→G; 861th: C→G; 864th: C→A; 888th: T→C; 897th: T→C; 900th: C→A; 906th: C→G; 912th: T→C; 924th: T→C; 936th: T→C; 939th: C→G; 942th; C→G; 948th: G→C; 949th: C→A; 951th: C→A; 955th: T→A; 956th: C→G; 957th: T→C; 963th: T→C; 978th: T→C; 1002th: A→G; 1005th: T→C; 1014th: A→C; 1017th: C→G; 1023th: G→C; 1026th: T→G; 1041th: T→C; 1047 th: T→C; 1053th: C→A; 1056th: C→G; 1062th: A→C; 1065th: A→C; 1066th; T→A; 1067th: C→G; 1072th: A→T; 1073th: G→C; 1080th: T→C; 1083th: T→C; 1089th: T→C; 1092th: A→C; 1095th: C→G; 1098th: T→C; 1101th: A→G; 1107th: C→T; 1110th: C→G; 1116th: A→G; 1119th: T→C; 1137th: A→C; 1143th: G→A; 1146th: A→G; 1149th: C→G; 1155th: T→C; 1159th: T→A; 1160th: C→G; 1167th: G→C; 1170th: C→G; 1171th: T→A; 1172th: C→G; 1173th: A→C; 1176th: C→G; 1185th: A→C; 1186th: T→A; 1187th: C→G; 1188th: G→C; 1197th: C→G; 1206th: A→C; 1209th: C→T; 1209th: C→T; 1213th: T→A; 1214th: C→G; 1215th: C→T; 1218th: A→T; 1224th: C→G; 1227th: A→C; 1233th: T→C; 1236th: C→G; 1239th: T→G; 1246th: T→A; 1247th: C→G; 1251th: C→T; 1257th: C→G; 1263th:

A→C; 1266th: C→G; 1278th: C→A; 1287th: A→C; 1297th: T→C; 1302th: A→C; 1308th: C→T; 1314th: G→C; 1326th: A→C; 1329th: G→T; 1335th: C→G; 1338th: C→G; 1341th: G→T; 1347th: A→G; 1350th: C→A; 1353th: G→C; 1356th: C→A; 1357th: T→C; 1362th: G→T; 1368th: G→T; 1381th: T→C; 1392th: G→C; 1401th: A→T; 1404th: C→A; 1420th: A→C; 1425th: C→G; 1431th: A→T; 1432: T→A, 1433th: C→G; 1434: G→C; 1435th: T→A; 1436th: C→G; 1437th; G→C, 1440th T→C; 1445th: C→A; 1447th: C→A; 1450th: C→T; 1456th: T→C; 1459th: C→G; 1462th: A→C; 1465th: C→G; 1468th: C→T; 1472th: T→A; 1473th: C→G; 1474th: T→C; 1480th: C→G; 1486th: C→T; 1489th: G→T; 1492th: T→C; 1495th: C→G; 1498th: C→G; 1501th: T→C; 1504th: T→C; 1511th: T→A; 1512th: C→G; 1519th: G→A; 1529th: T→A; 1530th: C→G; 1531th: A→C; 1534th: A→C; 1540th: C→T; 1544th: A→T; 1545th: G→C; 1546th: C→T; 1547th: C→A; 1552th: C→T; 1556th: T→C; 1558th: A→G; 1561th: T→C; 1573th: T→C; 1580th: T→A; 1581th: C→G; 1585th: T→C; 1588th: C→G; 1591th: T→C; 1597th: T→C; 1609th: G→C; 1618th: T→A; 1627th: C→T; 1630th: A→C; 1636th: C→G; 1651th: A→C; 1664th: C→A; 1666th: C→A; 1672th: C→A; 1681th: G→T; 1684th: A→C; 1685th: T→C; 1688th: T→C; 1702th: C→G; 1705th: A→T; 1706th: C→A; 1708th: G→A; 1717th: A→C; 1718th: T→A; 1719th: C→G; 1720th: A→C; 1732th: G→A; 1738th: A→G; 1753th: T→C; 1760th: T→C; 1765th: C→G; 1768th: G→A; 1771th: T→C; 1774th: T→C; 1777th: A→G; 1783th: C→G; 1789th: T→C; 1792th: A→C; 1825th: T→C; 1831th: T→C; 1834th: T→G; 1840th: T→C; 1844th: T→C; 1849th: G→C; 1855th: G→A; 1864th: G→A; 1867th: G→C; 1870th: T→C; 1873th: C→A; 1874th: T→A; 1875th: C→G; 1876th: T→C; 1891th: T→G; 1897th: T→C; 1900th: T→C; 1903th: T→C; 1906th: T→C; 1907th: C→A; 1909th: A→G; 1921th: G→A; 1927th: C→T; or 1930th: C→G.

In still other embodiment, the polynucleotide has a sequence as disclosed in SEQ ID NO: 2.

In other aspect, the present disclosure also provides a polypeptide encoded by the polynucleotide of the present disclosure.

In still other aspect the present disclosure provides a plasmid comprising the polynucleotide of the present disclosure and a promoter operatively linked to the nucleotide, wherein the plasmid is for the expression in a eukaryotic cell.

Also provided is a recombinant host cell comprising the plasmid and/or the polynucleotides in accordance with the present disclosure.

Also provided is a kit for radio-imaging, nuclear or molecular imaging comprising the plasmid of the present disclosure.

The foregoing summary is illustrative only and is not intended to be in any way limiting. Additional aspects and/or advantages of the invention will be set forth in part in the description which follows and; in part; will be obvious from the description; or may be learned by practice of the invention.

BRIEF DESCRIPTION OF THE DRAWINGS

These and/or other aspects and advantages of the invention will become apparent and more readily appreciated from the following description of the embodiments; taken in conjunction with the accompanying drawings of which:

FIG. 3b is a graph representing the result of FIG. 3a.

FIG. 7a is a comparison of nucleotide sequences of hNIS and oNIS from amino acids 1 through 660; in which Query indicates hNIS which is represented by SEQ ID NO:1; and Sbjct (subject) indicates oNIS, which is represented by SEQ ID NO:2. Further the amino acid sequences of oNIS encoded by SEQ ID NO: 2 is represented by SEQ ID NO: 3.

FIG. 7b is a comparison of nucleotide sequences of hNIS and oNIS from amino acids 661 through 1320; in which Query indicates hNIS which is represented by SEQ ID NO:1; and Sbjct (subject) indicates oNIS, which is represented by SEQ ID NO:2. Further the amino acid sequences of oNIS encoded by SEQ ID NO: 2 is represented by SEQ ID NO: 3.

FIG. 7c is a comparison of nucleotide sequences of hNIS and oNIS from amino acids 1321 through 1938; in which Query indicates hNIS; which is represented by SEQ ID NO:1; and Sbjct (subject) indicates oNIS, which is represented by SEQ ID NO:2. Further the amino acid sequences of oNIS encoded by SEQ ID NO: 2 is represented by SEQ ID NO: 3.

DETAILED DESCRIPTION OF THE EMBODIMENTS

Figure 1A:
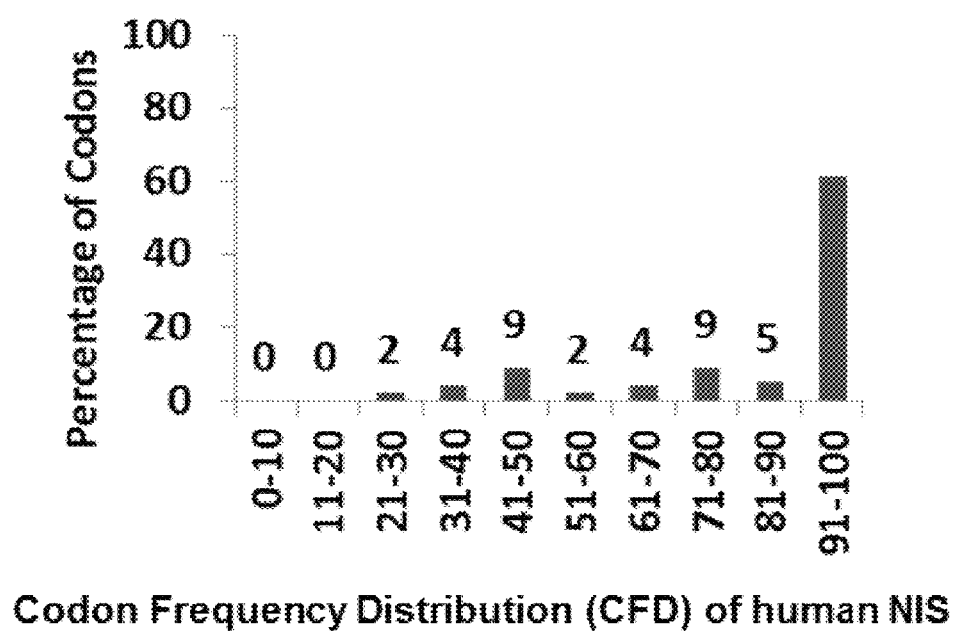
FIG. 1a is a codon frequency distribution (CFD) of human NIS.

In one aspect, the present invention is directed to enhancing the expression of a polynucleotide encoding an NIS (Sodium-Iodide Symporter), particularly derived from human being, by providing a polynucleotide comprising a codon-optimized coding region thereof, where the codons are optimized for eukaryotic cell expression.

As used herein the term "codon-optimized" or "codon-optimized coding region" means a nucleic acid coding region that has been adapted for expression in the eukaryotic cells of a given vertebrate by substituting, deleting and/or inserting at least one, or more than one, or a significant number, of codons with one or more codons that are more frequently used in the genes of that vertebrate, particularly in human.

Sodium Iodide Symporter (NIS) is a transmembrane glycoprotein with a MW of 87 kDa and 12 transmembrane domains; which transports two sodium cations for each iodide anion into cells. NIS mediated uptake of iodide into follicular cells of the thyroid gland is the first step in the synthesis of thyroid hormone resulting in 20-40 higher concentration of iodide in the thyroid.

The gene coding for NIS was first isolated in rats by Dai et al. (Dai et al.; Nature; 1996; 379: 458-460); followed by the isolation of Human NIS (hNIS) gene by Smanik et al. (Smanik et al.; Biochem. Biophysic. Res. Comm 226: 339-345; 1997).

Figure 7A:
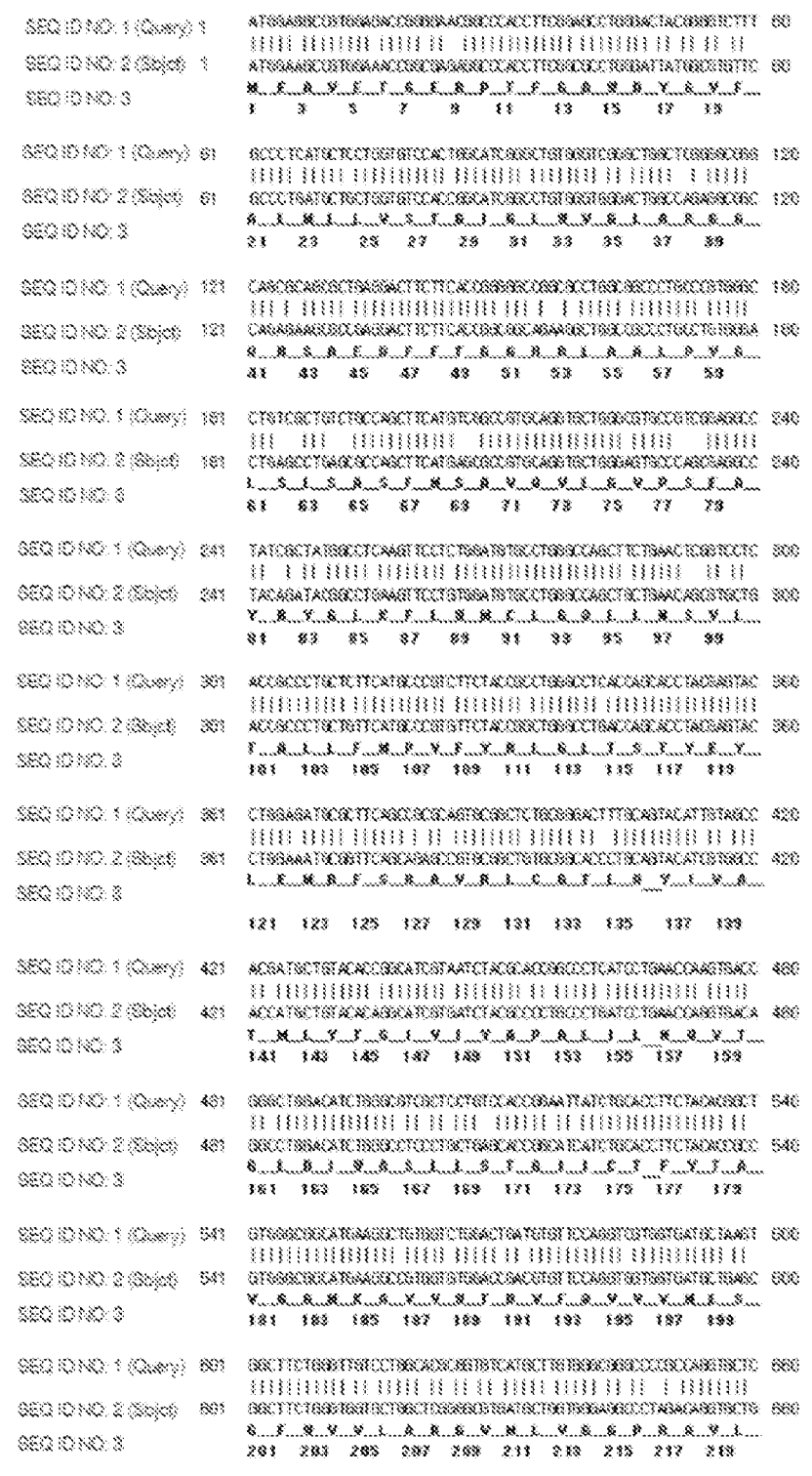
Figure 7B:
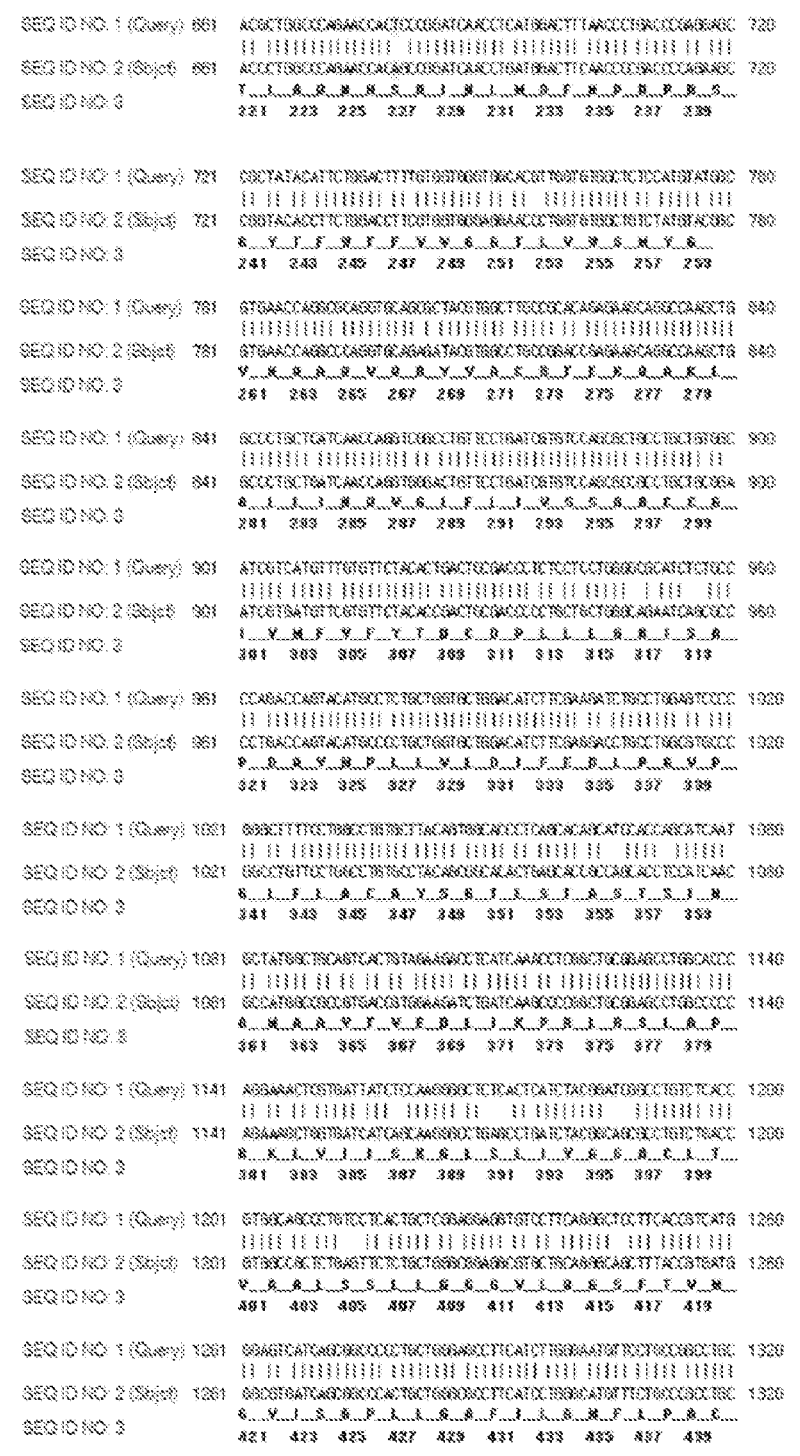
Figure 7C:
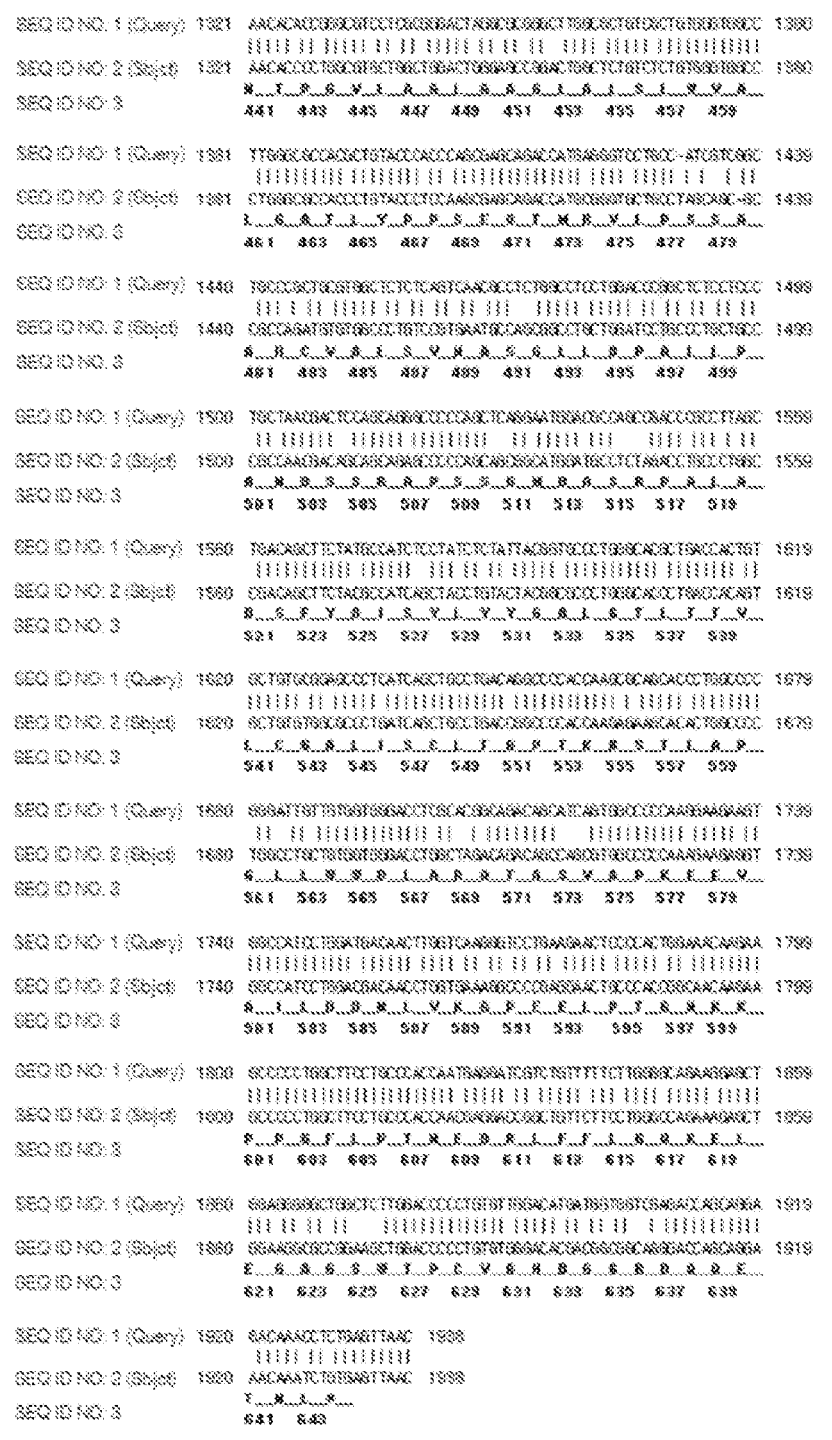

Genes for Sodium-Iodide Symporter which may be used for the present disclosure are derived from a mammal, particularly vertebrate, more particularly human being. Such sequences are known in the art and for example disclosed as NM_000435 for cDNA of SLC5A5 (Solute carrier family 5, sodium iodide symporter member 5) and GenBank No: AAB17378.1 for polypeptide. Further, the sequences as disclosed in FIGS. 7a through 7c may also be referred.

The polynucleotide is codon optimized in the nucleotides encoding the 8th transmembrane domain corresponding to amino acid residues 286-308 in SEQ ID NO:3; the $5^{th}$ transmembrane domain corresponding to 163-182 in SEQ ID NO:3; C-terminal region corresponding to 550-643 in SEQ ID NO:3; one or more of the phosphorylation sites of Ser-43, Thr-49, Ser-227, Lys-577, and Ala-581 in SEQ ID NO:3; and one or more of the N-glycosylation sites of Asn-225 Asn-489 and Asn-502 in SEQ ID NO:3.

In one embodiment, the codon optimized nucleotide sequence or coding region of a NIS is derived from the sequences as disclosed in FIG. 7 or SEQ ID NO: 1 and may include one or more of the substitution at the following site. The nucleotide numbers indicated below correspond to the nucleotide as disclosed in SEQ ID NO:1: 6th: G→A; 15 th: G→A; 22th: G→C; 24th: A→G; 25th: C→A; 39th: A→C; 48th: C→T; 51th: C→T; 54th: G→C; 57th: C→G; 60th: T→C; 66th: C→G; 72th: C→G; 84th: T→C; 93th: G→C; 102th: C→G; 105th: G→A; 111th: T→C; 112th: C→A; 114th: G→A; 120th: G→C; 124th: C→A; 126th: C→A; 132th: T→C; 150th: G→C; 154th: C→A; 156th: G→A; 157th: C→A; 159th: C→G; 165th: G→C; 174th: C→T; 180th: C→A; 184th: T→A; 185th: C→G; 186th: G→C; 190th: T→A; 191th: C→G; 192th: T→C; 205th; T→A; 206th: C→G; 207th: G→C; 225th: C→A; 231th: G→C; 232th: T→A; 233th: C→G; 234th: G→C; 243th: T→C; 244th: C→A; 246th: C→A; 249 th: T→C; 255th: C→G; 264th: C→G; 285th: T→G; 292th: T→A; 293th: C→G; 294th: G→C; 297th: C→G; 300th: C→G; 312th: C→G; 324th: C→G; 333th; C→G; 342th: G→C; 366th: G→A; 372th: C→G; 379th: C→A; 381th: C→A; 384th: A→C; 393th: C→G; 399th: G→C; 402th: T→C; 403th: T→C; 414 th: T→C; 417th: A→G; 423th: G→C; 435th: C→A; 444th: A→C; 456th: G→T; 462th: C→G; 474th: A→G; 480th: C→A; 483th: G→C; 498th: G→C; 501th: G→C; 504th: C→G; 508th: T→A; 509th: C→G; 516th: A→C; 519th: T→C; 537th: G→C; 540th: T→C; 558th: T→C; 564th: C→G; 570th: T→C; 573th: T→C; 585th: C→G; 597th: A→G; 600th: T→C; 612th: T→G; 615 th: C→G; 621th: A→T; 624th: C→G; 627th: T→C; 630th: C→G; 636th: T→G; 642th: C→A; 645th: G→C; 648th: C→T; 649th: C→A; 651th: C→A; 660th: C→G; 663th: G→C; 679th: T→A; 680th: C→G; 693th: C→G; 702th: T→C; 708th: T→C; 714th: G→C; 717th: G→A; 723th: C→G; 726th: T→C; 729th: A→C; 738th: T→C; 741th: T→C; 750th: T→A; 753th: C→A; 756th; G→C; 757th: T→C; 768th: C→G; 771th: C→T; 777th: T→C; 792th: G→C; 802th: C→A; 804th: C→A; 813th: T→C; 819th: C→G; 822th: A→C; 849 th: C→G; 861th: C→G; 864th: C→A; 888th: T→C; 897th: T→C; 900th: C→A; 906th: C→G; 912th: T→C; 924th: T→C; 936th: T→C; 939th: C→G; 942th; C→G; 948th: G→C; 949th: C→A; 951th: C→A; 955th: T→A; 956th: C→G; 957th: T→C; 963th: T→C; 978th: T→C; 1002th: A→G; 1005th: T→C; 1014th: A→C; 1017th: C→G; 1023th: G→C; 1026th: T→G; 1041th: T→C; 1047 the T→C; 1053th: C→A; 1056th: C→G; 1062th: A→C; 1065th: A→C; 1066th; T→A; 1067th: C→G; 1072th: A→T; 1073th: G→C; 1080th: T→C; 1083th: T→C; 1089th: T→C; 1092th: A→C; 1095th: C→G; 1098th: T→C; 1101th: A→G; 1107th: C→T; 1110th: C→G; 1116th: A→G; 1119th: T→C; 1137th: A→G; 1143th: G→A; 1146th: A→G; 1149th: C→G; 1155th: T→C; 1159th: T→A; 1160th: C→G; 1167th: G→C; 1170th: C→G; 1171th: T→A; 1172th: C→G; 1173th: A→C; 1176th: C→G; 1185th: A→C; 1186th: T→A; 1187th: C→G; 1188th: G→C; 1197th: C→G; 1206th: A→C; 1209th: C→T; 1209th: C→T; 1213th: T→A; 1214th: C→G; 1215th: C→T; 1218th: A→T; 1224th: C→G; 1227th: A→C; 1233th: T→C; 1236th: C→G; 1239th: T→G; 1246th: T→A; 1247th: C→G; 1251th: C→T; 1257th: C→G; 1263th: A→C; 1266th: C→G; 1278th: C→A; 1287th: A→C; 1297th: T→C; 1302th: A→C; 1308th: C→T; 1314th: G→C; 1326th: A→C; 1329th: G→T; 1335th: C→G; 1338th: C→G; 1341th: G→T; 1347th: A→G; 1350th: C→A; 1353th: G→C; 1356th: C→A; 1357th: T→C; 1362th: G→T; 1368th: G→T; 1381th: T→C; 1392th: G→C; 1401th: A→T; 1404th: C→A; 1420th: A→C; 1425th: C→G; 1431th: A→T; 1432: T→A, 1433th: C→G; 1434: G→C; 1435th: T→A; 1436th: C→G; 1437th; G→C, 1440th T→C; 1445th: C→A; 1447th: C→A; 1450th: C→T; 1456th: T→C; 1459th: C→G; 1462th: A→C; 1465th: C→G; 1468th: C→T; 1472th: T→A; 1473th: C→G; 1474th: T→C; 1480th: C→G; 1486th: C→T; 1489th: G→T; 1492th: T→C; 1495th: C→G; 1498th: C→G; 1501th: T→C; 1504th: T→C; 1511th: T→A; 1512th: C→G; 1519th: G→A; 1529th: T→A; 1530th: C→G; 1531th: A→C; 1534th: A→C; 1540th: C→T; 1544th: A→T; 1545th: G→C; 1546th: C→T; 1547th: C→A; 1552th: C→T; 1556th: T→C; 1558th: A→G; 1561th: T→C; 1573th: T→C; 1580th: T→A; 1581th: C→G; 1585th: T→C; 1588th: C→G; 1591th: T→C; 1597th: T→C; 1609th: G→C; 1618th: T→A; 1627th: C→T; 1630th: A→C; 1636th: C→G; 1651th: A→C; 1664th: C→A; 1666th: C→A; 1672th: C→A; 1681th: G→T; 1684th: A→C; 1685th: T→C; 1688th: T→C; 1702th: C→G; 1705th: A→T; 1706th: C→A; 1708th: G→A; 1717th: A→C; 1718th: T→A; 1719th: C→G; 1720th: A→C; 1732th: G→A; 1738th: A→G; 1753th: T→C; 1760th: T→C; 1765th: C→G; 1768th: G→A; 1771th: T→C; 1774th: T→C; 1777th: A→G; 1783th: C→G; 1789th: T→C; 1792th: A→C; 1825th: T→C; 1831th: T→C; 1834th: T→G; 1840th: T→C; 1844th: T→C; 1849th: G→C; 1855th: G→A; 1864th: G→A; 1867th: G→C; 1870th: T→C; 1873th: C→A; 1874th: T→A; 1875th: C→G; 1876th: T→C; 1891th: T→G; 1897th: T→C; 1900th: T→C; 1903th: T→C; 1906th: T→C; 1907th: C→A; 1909th: A→G; 1921th: G→A; 1927th: C→T; or 1930th: C→G.

In other embodiment, the polynucleotide of the present disclosure is disclosed as SEQ ID NO:2.

In other aspect, the present disclosure is directed to a polypeptide encoded by NIS polynucleotide which is codon-optimized for expression in eukaryotic cells. In one embodiment, there are no changes in the amino acid sequence by the optimized codons.

Further the present disclosure is directed to a plasmid for eukaryotic expression comprising a polynucleotide of the present disclosure and a promoter operatively linked thereto.

The plasmid of the present disclosure is to express oNIS of the present disclosure in eukaryotic cells. Thus, a variety of promoters may be utilized for the present purpose. For example, EF-1 Alpha promoter (Clontech, USA), Ubiquitin promoter (Christensen A H et al., Transgenic Res. 1996; 5(3)-213-8), CMV promoter (cytomegalovirus promoter) (Clontech, USA), LTR (Retroviral promoter) (Reynolds et al., PNAS 2003; 100(4):1615-1620) and beta-actin promoter (Clontech, USA) may be used for the present disclosure without being limited thereto.

In other aspect, the present disclosure is directed to a recombinant eukaryotic cell, particularly cells derived from a mammal, more particularly cells derived from a human being comprising the plasmid of the present disclosure. In one embodiment, the cells are derived from a human cancer. A variety of eukaryotic cells known in the art which may be transfected with the present plasmids may be used for the present purpose. For example it includes cancer cell lines such as thyroid cancer, liver cancer, glioma, cervical cancer and the like. Particularly, it includes MDA-MB-231, TPC-1, FRO, BCRAP, HEP3B, HeLa and U87MG without being limited thereto. Further, breast cancer cell lines such as MCF7, MDAMB468 and KPL4, colon cancer cell lines such as HT29, Caco-2, HCT116, and lung cancer cell lines such as A549 and NCI-H446 may also be used.

A variety of transfection methods known in the art may be used for the present disclosure, and includes, but are not limited to, calcium phosphate precipitation methods, electroporation, liposome and shot-gun methods and the like.

In a further aspect, the present disclosure is directed to a kit comprising a codon optimized polynucleotide encoding NIS and/or a plasmid comprising the same for nuclear and/or molecular imaging or for imaging reporter for gene, viral and cell based therapies. The codon optimized polynucleotides of the present disclosure which are included in the kit are optimized for the efficient expression and functional activities in eukaryotic cells and thus can be utilized for the development as a gene therapy vector, a reporter for nuclear and/or molecular imaging, and a transgenic mouse overexpressing a gene for molecular imaging using radionuclides such as Iodide $^{123,124,125,131}$I, Rhenium $^{186,188}$RE, technetium $^{99m}$Tc and the like. The kits are useful as a reporter for imaging, for combined cancer therapy of radioactive iodide with gene therapy and for thyroid cancer therapy using radioactive iodide.

The present disclosure is further explained in more detail with reference to the following examples. These examples; however; should not be interpreted as limiting the scope of the present invention in any manner.

EXAMPLES

Example 1

Construction of a Codon Optimized NIS and a Plasmid Comprising the Same

For the construction of a codon optimized NIS, the following regions of a NIS were selected: the 8$^{th}$ transmembrane domain from the N-terminal recognizing iodide (amino acid residues 286-308) and the 5$^{th}$ transmembrane domain (163-182) involved in the membrane penetration, and C-terminal region (550-643). Further the sites which are important for the functional activity of NIS, i.e., phosphorylation sites, Ser-43, Thr-49, Ser-227, Lys-577 and Ala-581 which are modified post-translationally and N-glycosylation sites Asn-225 Asn-489 and Asn-502 were selected for the modification.

Codon optimizing software (GENEOPTIMIZER™ GENEART®" Life Technologies) was used to obtain a modified sequence, which were then synthesized in Takara Bio Inc. (JAPAN).

The results of substitutions are summarized in Table 1, FIGS. 1a through 1e.

TABLE 1

| | CDS length | Amino acid | Codon Adaptation Index m(CAI) | Codon Frequency Distribution |
|---|---|---|---|---|
| hNIS | 1932 bp | 643 | 0.79 | 61% |
| oNIS | 1932 bp | 643 | 0.97 | 88% |

Table 1 is the comparison of the parent sequence of NIS and the modified sequences thereof in various aspects as indicated. Both have the same length of coding region of 1932 by encoding 643 amino acids.

For analyzing codon usage bias, Codon Adaptation Index (CAI) which measures the deviation of a given protein coding gene sequence with respect to a reference set of genes was determined. As shown in FIGS. 1c to 1e, CAI was found to be 0.79 in the parent sequence of NIS in contrast to 0.97 in the modified sequence. Further the amount of GC content was found to be 64%.

Figure 1B:
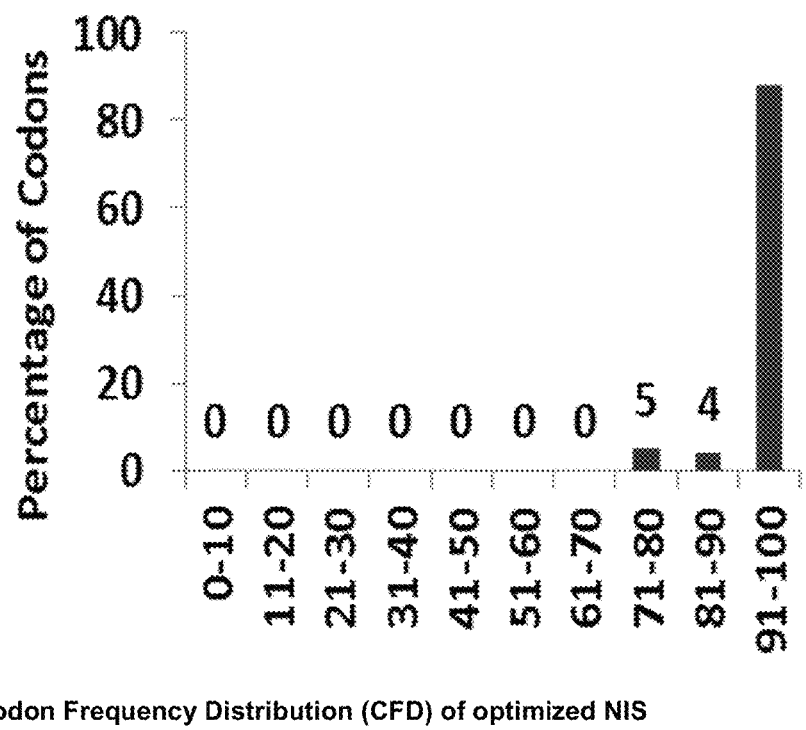
FIG. 1b is a codon frequency distribution of optimized NIS (oNIS) in accordance with the present disclosure.
Figure 1C:
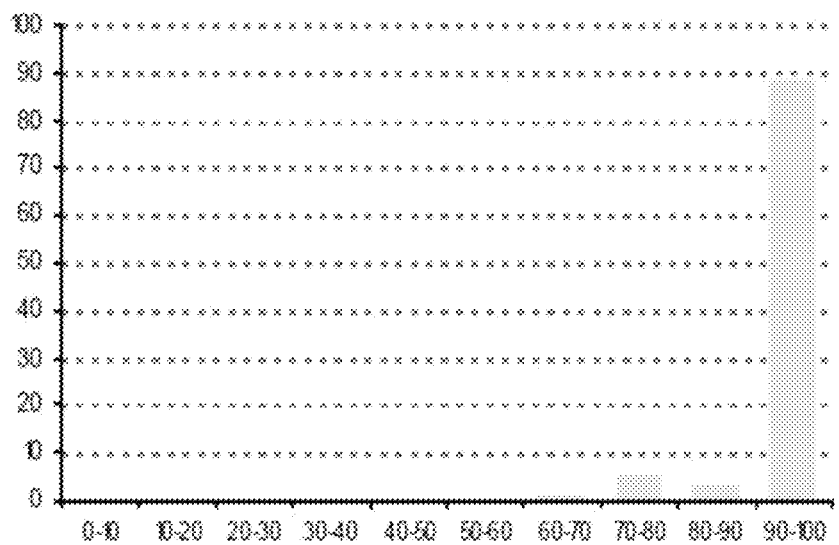
FIG. 1c is a graph showing the codon quality distribution of the oNIS in accordance with the present disclosure.
Figure 1D:
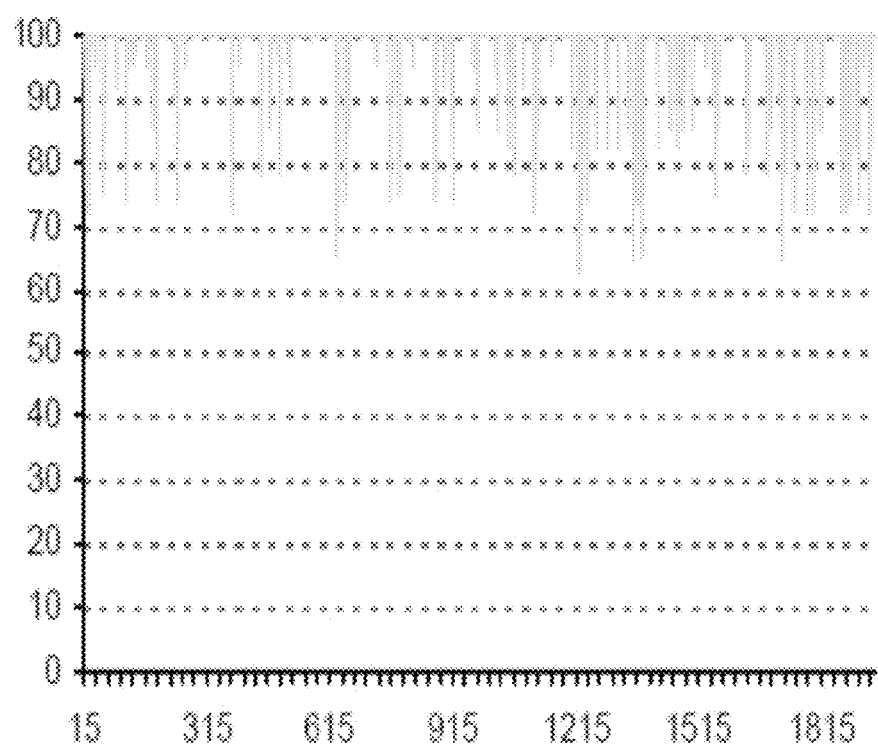
FIG. 1d is a graph showing the codon quality plot of the oNIS in accordance with the present disclosure.
Figure 1E:
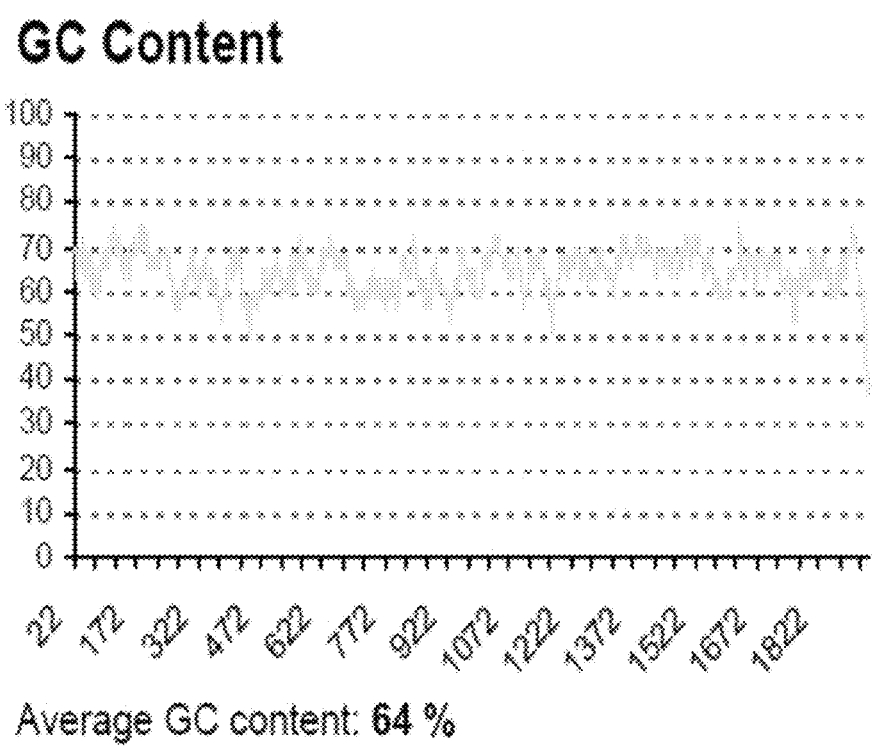
FIG. 1e is a graph showing the GC content of the oNIS in accordance with the present disclosure. The codon with a highest frequency for each amino acid was given a value of 100 and; the histogram represents the percent of codons that meets a given value that determines the quality.

Further according to the codon frequency graph as shown in FIGS. 1a and 1b, the percent of codons which are utilized with 91-100% frequency was found to be 61% in the parent sequence of NIS in contrast to 88% in the modified sequence.

Figure 2:
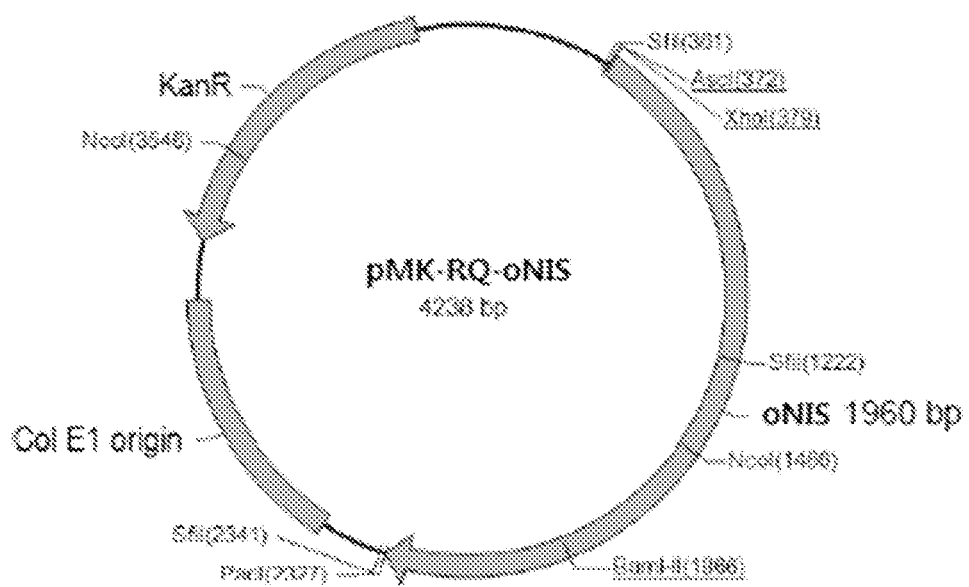
FIG. 2 is an illustrative map of the recombinant plasmid having oNIS according to one embodiment of the present disclosure

Then the modified DNA fragment was then cloned into a cloning vector and a eukaryotic expression vector to construct a plasmid comprising the modified NIS DNA.

pMK-RQ (Invitrogen Inc. USA) was used as a cloning vector and the modified DNA was cloned into NcoI and SfiI restriction sites to obtain a pMK-RQ-oNIS, the map of which is shown in FIG. 2.

For the expression in human cells, the modified DNA, oNIS and hNIS each was cloned into each of a vector, PCDNA™3.1 (Invitrogen Inc. USA) and pMSCV (Clontech Laboratories, Inc. USA) at XhoII/ApaI restriction site to obtain expression plasmids, PCDNA™3.1-oNIS, PCDNA™3.1-hNIS, pMSCV-oNIS and pMSCV-hNIS.

Example 2

Determination of Expression Level of Codon Optimized NIS in Cells

Each of pMSCV-oNIS and pMSCV-hNIS as constructed in Example 1 was transfected into a breast cancer cell line MDA-MB-231 (ATCC® HTB-26™). The vectors are based on retroviral DNA and the viruses were prepared in a renal cell line FT293 (Life Technologies, Invitrogen) one day before the transfection. The amount of plasmid used for the transfection was 1 μg, 1 μg, and 2 μg for gag/pol, envelope, pMSCV-oNIS/pMSCV-hNIS, respectively. The plasmids were dissolved in 750 μl of OPTI-MEM® as a medium (Invitrogen Inc.), which was then mixed with 30 μg of LIPO-FECTAMINE® 2000 (Invitrogen Inc.) as a transfection agent and incubated for 15 min at RT. The mixture was then added to the FT293 cells prepared as above and incubated for 48 hours. Then the supernatant containing the viruses was collected and 1 ml of the supernatant per 5 ml of the cell culture medium containing 10 μg/mL of polybrene was used to infect MDA-MB-231 cells and incubated for 48 hours. Subsequently 2 μg/mL of puromycin (Invitrogen Inc.) was added to select the resistant cells and to obtain a stable cell line. For 2 weeks after the transfection, the cells were cultured at 37° C., 5% $CO_2$ and 95% humidity, which were then analyzed for the expression of NIS using Reverse transcription PCR (RT-PCR) and western blot. As a reference, GAPDH and beta-actin were used.

For RT-PCR, total RNA was extracted from the cells using TRIZOL® (Invitrogen Inc.) as an RNA extraction agent according to the manufacturer's instruction and cDNA was synthesized using oligo dT and cDNA synthesis kit (amfiRivert Platinum cDNA Synthesis Master Mix (GenDEPOT, USA). Subsequently cDNA was amplified using the following primers: for NIS amplification (F'-TGGGCGGCAT-GAAGGCYGTG: SEQ ID NO: 4, R'-CRCTGTAGGCA-CAGGCCAGG: SEQ ID NO: 5), for GAPDH primer (F'-GAGAAGGCTGGGGCTCATTT: SEQ ID NO: 6, R'-CCTTCCGTGTCCCCACTG: SEQ ID NO: 7), and under the following condition: 5 min at 94° C. for denaturation; 30 cycles of 30 sec at 94° C. 30 sec at 56.5° C. or 60° C.; 30 sec at 72° C.; and a final step for 7 min at 72° C.

For western blot analysis, whole protein was extracted using RIPA buffer Sigma Aldrich, USA) according to the manufacturer's instruction. Then 30 μg of protein extract was electrophoresed on a 12% Bis-Tris gel NUPAGE®, Invitrogen) at 150V for 2 hours and transferred to a PVDF membrane (Invitrogen) at 70V for 3 hours. The membrane was then incubated with anti-hNIS (KOMA Biotech, Korea) at 1:1000 dilution overnight at 4° C. followed by an incubation with a second antibody, anti-rabbit-IgG (KOMA Biotech, Korea) at 1:2000 dilution for 2 hours at RT and visualized using PIERCE™ ECL Western Blotting Substrate (Thermo Scientific, USA) as a substrate according to the manufacturer's instruction.

Figure 3A:
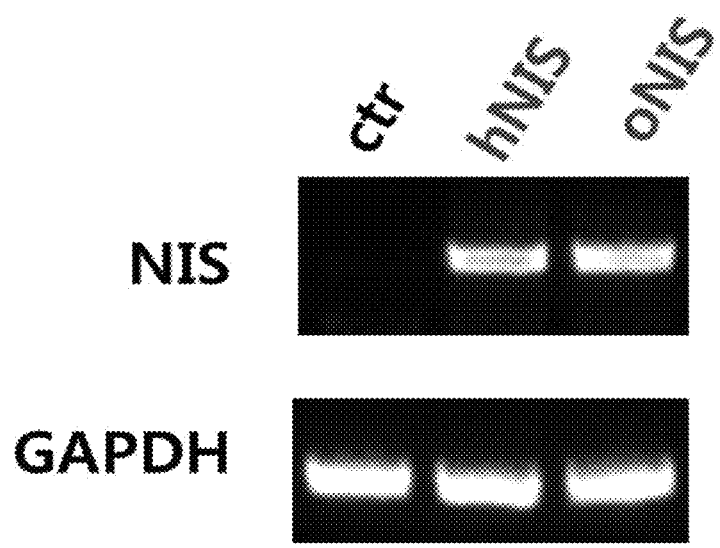
FIG. 3a is a RT-PCR analysis result in which the expression of hNIS was compared to that of the control (CTR) using the cells transfected with a plasmid having oNIS.
Figure 3B:
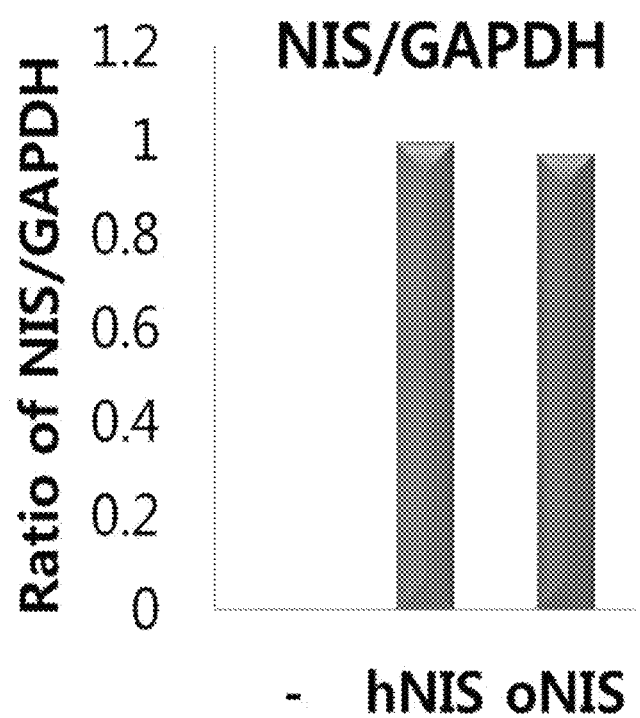
Figure 3C:
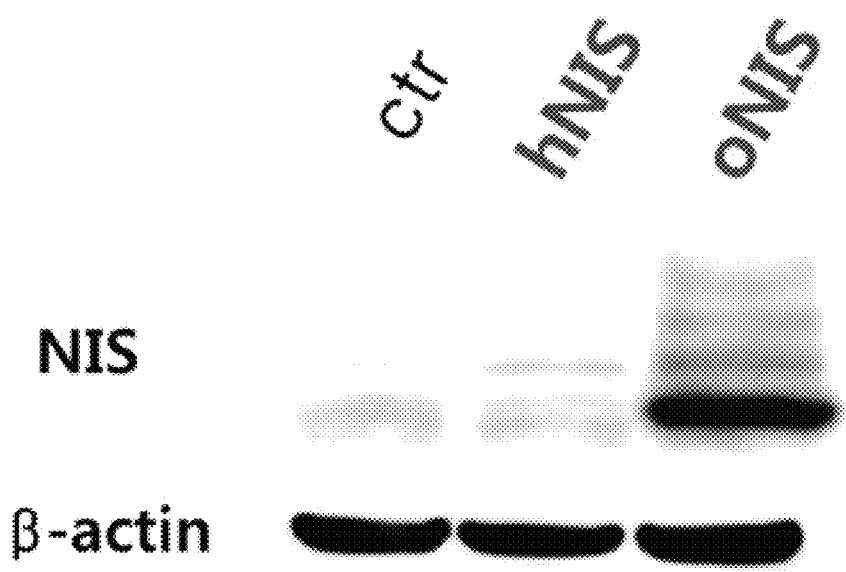
FIG. 3c is a western blot result in which the expression of hNIS was compared to that of the control (CTR) using the human breast cancer cell line transfected with a plasmid having oNIS.
Figure 3D:
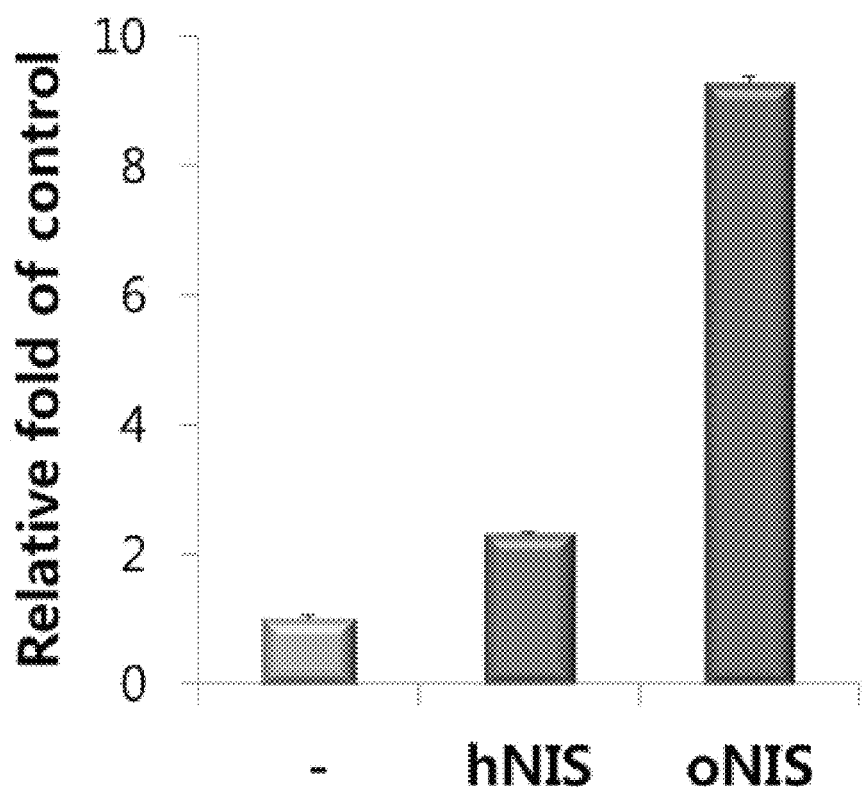
FIG. 3d is a graph representing the result of FIG. 3c.

Results are shown in FIGS. 3a through 3d. As shown in FIGS. 3a and 3b, at the mRNA level, it has been found that there was no difference between hNIS and oNIS. However, as shown in FIGS. 3c and 3d, at the protein level, it has been found that the expression level of oNIS was four times higher than that of hNIS. This indicates that the protein expression can be significantly increased by the codon-optimized NIS according to the present disclosure.

Example 3

Determination of Radioactive Iodine Uptake in Various Human Cancer Cell Lines

Example 3-1

Cancer Cell Lines and Transfection

TPC-1 and FRO (Donated by Dr. Shunichi Yamashita, Nagasaki University) were cultured in RPMI 1640 (Promega, USA) supplemented with 5% non-heat inactivated fetal bovine serum and 1% antibiotic-antimycotic at 37° C. in 5% $CO_2$. B-CPAP (Donated by Dr. Shunichi Yamashita, Nagasaki University; Leibniz Institute DSMZ German Collection of Microorganisms) cells were grown under the same condition as described above except that 10% heat inactivated fetal bovine serum was used. HEP3B and Hela (Korean Cell Line Bank, Korea) were grown in DMEM (Dulbecco's Modified Eagle Medium) supplemented with 10% heat inactivated fetal bovine serum and 1% antibiotic-antimycotic at 37° C. in 5% $CO_2$. U87MG(ATCC) was grown in MEM (Minimum Essential Medium) supplemented with 10% heat inactivated fetal bovine serum and 1% antibiotic-antimycotic at 37° C. in 5% $CO_2$. The cell lines described above have the following origin as described in Table 2.

TABLE 2

| Cell Line | Origin |
| --- | --- |
| TPC-1 | Thyroid cancer (Papillary) |
| FRO | Thyroid cancer (Anaplastic) |
| B-CPAP | Thyroid cancer (Papillary) |
| HEP3B | Liver cancer |
| HeLa | Cervical Cancer |
| U87MG | Glioma |

For the transfection, each of the cell lines as described above was transfected with 20 μg of each of a vector PCDNA™3.1-hNIS and PCDNA™3.1-oNIS using LIPO-FECTAMINE®2000 (Invitrogen) as a transfection agent according to the manufacturer's instructions. The stable cell lines were established as described in Example 2 for MDA-MB231 cell line.

Example 3-2

Comparison of the Uptake of Radioactive Iodide in Various Human Cancer Cell Lines The cells transfected in Example 3-1 were treated with radioactive iodide, Na $^{125}$I (Perkin Elmer, USA). Specifically, the cells were seeded onto each well of a 24 well plate at $3\times10^5$ cells/well and 37 kBq/ml of Na $^{125}$I was added to each well and incubated for 30 min at 37° C. in 5% $CO_2$. Then the cells were lysed using sodium dodecyl sulfate and the radioactivity therefrom was measured using a gamma counter. The amount of protein in each sample was measured using BCA assay kit (Pierce Biotechnology, USA) according to the manufacturer's instruction and used to normalize the results as pmol/mg. Also the cells were photographed with a gamma camera (γ-ray camera (ON-410); Ohio Nuclear, Solon, Ohio, USA) for 300 k counts.

Figure 4:
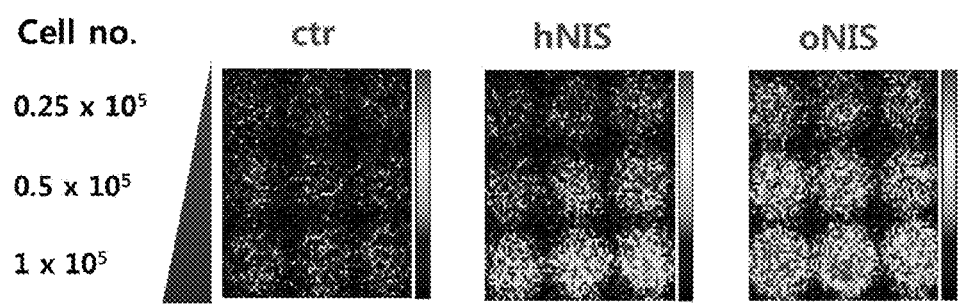
FIG. 4 is an image of a gamma camera showing the uptake of radioactive iodide by the human breast cancer cell line transfected with hNIS or control.
Figure 5:
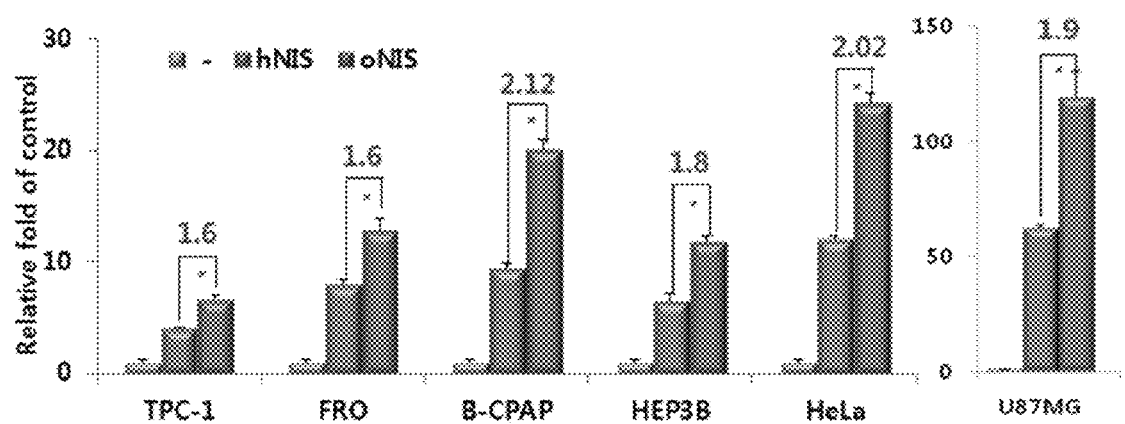
FIG. 5 is a result comparing the uptake of radioactive iodide in a variety of human breast cancer cell lines.

Results are shown in FIGS. 4 and 5. FIG. 4 is a gamma camera image showing the uptake of radioactive iodides in human breast cancer cell line transfected with oNIS as compared with controls (CRT, hNIS). FIG. 5 shows the uptake of radioactive iodide in various cancer cell lines transfected with control, hNIS or oNIS polynucleotides. The results indicate that the cells expressing oNIS have a higher uptake of radioactive iodide compared to the cells expressing hNIS.

Example 3-3

Comparison of the Uptake of Radioactive Iodide in a Human Cancer Cell Line and a Mouse Implanted Therewith Cells stably transfected with oNIS or hNIS polynucleotides prepared in Example 3-1 were seeded onto each well of a 24 well plate at $3\times10^5$ cells/well and treated with 3.7 mBq/ml of $^{99m}$Tc and incubated for 30 min at 37° C. in 5% $CO_2$. Then the cells were lysed with SDS and photographed with gamma camera. Also each of the stably transfected cells expressing oNIS or hNIS were implanted into the hind limb of Balb/Nude mouse (Oriental Bio, Korea) at $5\times10^6$ cells/site.

After 2 weeks, the mouse were treated with 500 μCi (18.5 mBq) of $^{99m}$Tc and photographed with a gamma camera as described above.

Figure 6A:
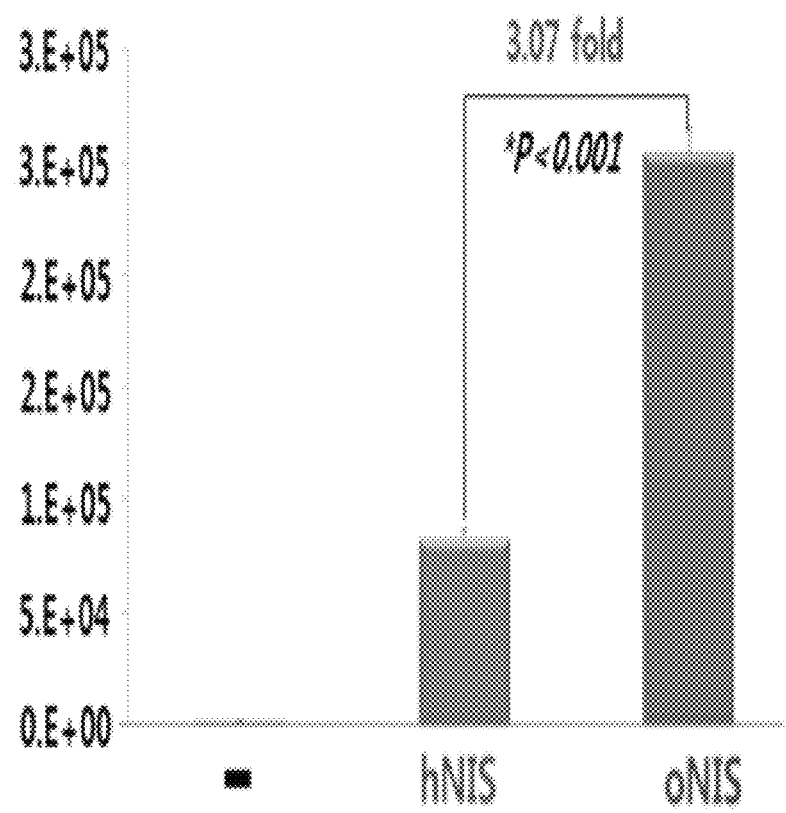
FIG. 6a is a result comparing the uptake of hNIS/oNIS radioactive iodide in a human breast cancer cell line transfected with hNIS or oNIS.
Figure 6B:
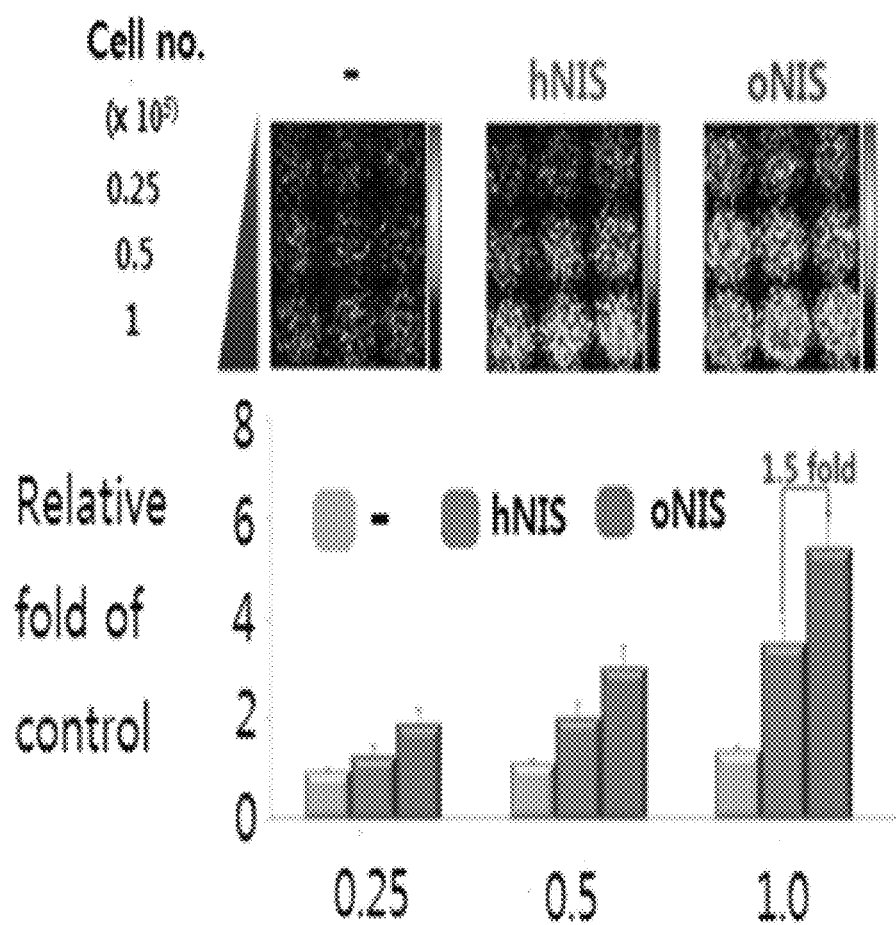
FIG. 6b is an image of a gamma camera showing the uptake of radioactive iodide by the human breast cancer cell line transfected with hNIS or oNIS.
Figure 6C:
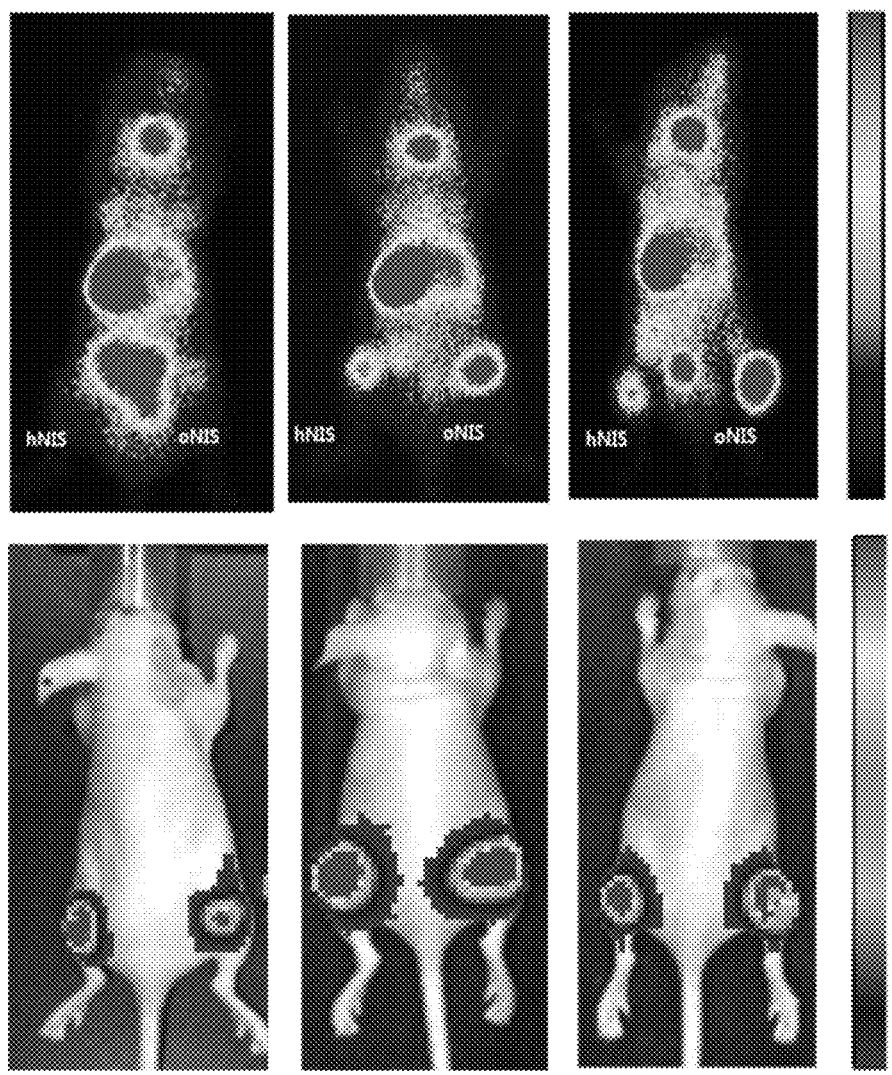
FIG. 6c is an image of a gamma camera comparing the uptake of hNIS/oNIS radioactive by the mouse injected with human breast cancer cells expressing hNIS or oNIS.
Figure 6D:
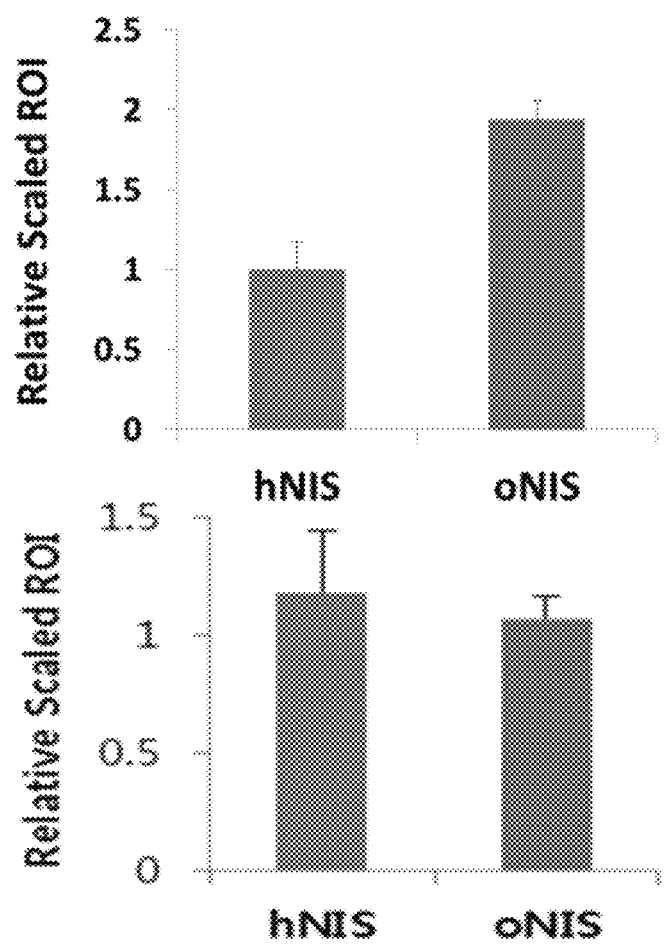
FIG. 6d is a result comparing the uptake of hNIS/oNIS radioactive $^{99m}Tc$ by the mouse implanted with human breast cancer cells expressing hNIS or oNIS.

Results are shown in FIGS. 6a through 6d. As shown in FIG. 6a, the cells expressing oNIS have about three times higher uptake of radioactive iodide than that of the cells expressing hNIS. As shown in FIG. 6b, the results from gamma camera analysis show 1.5 times increase in the radioactivity. Also as shown in FIGS. 6c and 6d, it has been found that the uptake of $^{99m}$Tc was increased in the tumor expressing oNIS compared to that expressing hNIS, in which both tumor had the same size. This indicates the excellent efficiency of the optimized codon in the translation into proteins.

Sequence Listing submitted in txt format (.txt) filed on Jun. 18, 2013 named "SequenceListing_YOUN.txt" (created on Jun. 17, 2013; KN); is incorporated herein by reference.

The various singular/plural permutations may be expressly set forth herein for sake of clarity. Although a few embodiments of the present disclosure have been shown and described; it would be appreciated by those skilled in the art that changes may be made in this embodiment without departing from the principles and sprit of the invention; the scope of which is defined in the claims and their equivalents

What is claimed is:

1. A polynucleotide encoding a sodium-iodide symporter (NIS) protein having the sequence set forth in SEQ ID NO: 2 and codon optimized for expression in a eukaryotic cell.

2. A plasmid comprising the polynucleotide of claim 1 and a promoter operatively linked to the polynucleotide, wherein the plasmid is codon optimized for expression in a eukaryotic cell.

3. An isolated recombinant host cell comprising the plasmid of claim 1 or the polynucleotide of claim 4.

4. The isolated recombinant cell of claim 3, wherein the cell is a mammal cell.

5. The isolated recombinant cell of claim 3, wherein the cell is a human cell.

6. The isolated recombinant cell of claim 3, wherein the cell is a non-human mammal cell.

7. A kit for radio-imaging, nuclear medicine imaging or molecular imaging comprising the plasmid of claim 2.

* * * * *

UNITED STATES PATENT AND TRADEMARK OFFICE
CERTIFICATE OF CORRECTION

PATENT NO. : 9,096,867 B2
APPLICATION NO. : 13/920692
DATED : August 4, 2015
INVENTOR(S) : Hyewon Youn Page 1 of 1

It is certified that error appears in the above-identified patent and that said Letters Patent is hereby corrected as shown below:

In the claims

Claim 3, Column 19, Line 42:

delete "of claim 1 or the polynucleotide of claim 4."

and replace with -- of claim 2 or the polynucleotide of claim 1. --

Signed and Sealed this
Fifteenth Day of December, 2015

Michelle K. Lee
*Director of the United States Patent and Trademark Office*